United States Patent [19]

Sugano et al.

[11] Patent Number: 5,449,650
[45] Date of Patent: Sep. 12, 1995

[54] CATALYST COMPONENTS FOR POLYMERIZATION OF OLEFINS AND USE THEREOF

[75] Inventors: Toshihiko Sugano; Tomohiko Takahama, both of Yokkaichi, Japan

[73] Assignee: Mitsubishi Petrochemical Company Limited, Tokyo, Japan

[21] Appl. No.: 161,464

[22] Filed: Dec. 6, 1993

[30] Foreign Application Priority Data

Dec. 8, 1992 [JP] Japan .................................. 4-328211
Dec. 8, 1992 [JP] Japan .................................. 4-328225

[51] Int. Cl.$^6$ .......................... B01J 31/14; B01J 21/02
[52] U.S. Cl. .................................. 502/117; 502/103; 502/202; 502/263
[58] Field of Search ................ 502/202, 263, 103, 117

[56] References Cited

U.S. PATENT DOCUMENTS

| | | | |
|---|---|---|---|
| 5,001,244 | 3/1991 | Welborn, Jr. ................ | 556/53 |
| 5,104,838 | 4/1992 | Fujita et al. .................. | 502/108 |
| 5,126,303 | 6/1992 | Resconi et al. ................ | 502/117 |
| 5,354,721 | 10/1994 | Geerts .......................... | 502/117 |

FOREIGN PATENT DOCUMENTS 1289811 5/1988 Japan .
WO92/01005 1/1992 WIPO .

*Primary Examiner*—P. Achutamurthy
*Assistant Examiner*—Timothy H. Meeks
*Attorney, Agent, or Firm*—Oblon, Spivak, McClelland, Maier & Neustadt

[57] ABSTRACT

Disclosed is a catalyst component for the polymerization of olefins, which is a compound having the following structure:

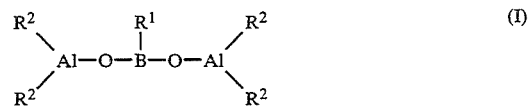

(I)

wherein $R^1$ is a hydrocarbon radical having 1 to 10 carbon atoms or a halogen-containing hydrocarbon radical having 1 to 10 carbon atoms, and $R^2$s are each a hydrogen atom, a halogen atom, a siloxy group, a lower-alkyl-substituted siloxy group or a hydrocarbon radical having 1 to 10 carbon atoms, or which is a reaction product of the following sub-components (i) and (ii):

sub-component (i) which is a compound having the formula $$R^1\text{-B-(OH)}_2$$

in which $R^1$ is a hydrocarbon radical having 1 to 10 carbon atoms or a halogen-containing hydrocarbon radical having 1 to 10 carbon atoms; and sub-component (ii) which is an organoaluminum compound.

3 Claims, 4 Drawing Sheets

CATALYST COMPONENTS FOR POLYMERIZATION OF OLEFINS AND USE THEREOF

BACKGROUND OF THE INVENTION

1. Field of the Art

The present invention relates to catalyst components useful for the polymerization of olefins. More specifically, the present invention relates to catalyst components for the polymerization of olefins, comprising an organoaluminum compound component having a specific structure. Further, the present invention relates to catalysts for the polymerization of α-olefins, comprising an organoaluminum compound component having a specific structure and a transition-metal compound having at least one conjugated 5-membered cyclic ligand where the transition metal belongs to one of the groups IVB to VIB in the Periodic Table; and to a method for preparing α-olefin polymers, comprising the step of bringing an α-olefin into contact with the catalyst to polymerize the α-olefin.

2. Related Art

A method for preparing α-olefin polymers in which alumoxane and a transition-metal compound are used in combination is well known (Japanese Laid-Open Patent Publications Nos. 45205/1983, 19309/1983, 35007/1985, 130314/1986, 230802/1987, 142004/1988, 234009/1988, 51408/1989 and 66214/1989 ). However, judging from an industrial point of view, the above technique seems to have some problems, because the activity per aluminum atom may be low, so that the production cost may be high, and a large amount of aluminum may remain in the olefin polymers produced.

Various proposals have been made in order to solve the above problems (Japanese Laid-Open Patent Publications Nos. 211307/1986, 130601/1988, 16803/1989, 22308/1990 and 167307/1990). By these proposals, the activity per aluminum atom has been improved to some extent. However, since the alumoxanes used in these proposals may have poor solubility, they may be inconvenient in handling. In addition, it may be difficult to remove aluminum from the olefin polymers produced, resulting in deterioration of the quality and the hue of the polymers. It is therefore considered that these proposals may still require further improvement.

Another proposal provides a method in which methylalumoxane is used together with another organoaluminum compound (Japanese Laid-Open Patent Publications Nos. 260602/1985, 130604/1985, 89506/1988, 178108/1988, 218707/1988, 9206/1989, 315407/1989, 22306/1990 and 167310/1990). The amount of alumoxane to be used may be decreased by this proposal. However, the activity per aluminum atom would still be insufficient, so that further improvement may be required.

On the other hand, a catalyst component for the polymerization of olefins, comprising an alumoxane compound having two or more types of alkyl groups has been proposed as a new attempt (Japanese Laid-Open Patent Publications Nos. 247201/1990, 250886/1990, 46906/1992, 26410/1992 and 266910/1992). Further, there is also a proposal in which an alumoxane compound obtained by substituting a part of the alkyl groups contained in the above alumoxane compound with hydrogen is employed (Japanese Laid-Open Patent Publication No. 139503/1991). However, all of these alumoxane compounds have a high association degree, so that it may be necessary to use a large amount of the alumoxane compounds in order to maintain high activity. Moreover, they are soluble only in an aromatic solvent, so that they would have many industrial restrictions.

The use of a tetraalkylalumoxane compound has been proposed so as to obtain polymers having lowered molecular weight (Japanese Laid-Open Patent Publication No. 197514/1991). This alumoxane compound is advantageous in that it is readily soluble also in an aliphatic hydrocarbon solvent. However, although this alumoxane compound reveals high activity when used for the polymerization of ethylene, it may exhibit extremely low activity when used for the polymerization of α-olefins such as propylene. Therefore, this proposal may also require further improvement.

Reaction products of an organoaluminum compound and an oxygen-supplying compound other than water (for instance, boroxine or alkyltin oxide) have been proposed (Japanese Laid-Open Patent Publications Nos. 256686/1990, 304202/1992, 304203/1992 and 304206/1992). However, the products obtainable by any of the methods described in these publications are alumoxanes having an Al-O-Al bond, so that they seem to have the same problems as the above.

On the other hand, reaction products of a dihydric alcohol or a primary amine and an organoaluminum compound have been proposed as organoaluminum compounds other than alumoxane compounds (Japanese Laid-Open Patent Publication No. 62806/1991). However, the organoaluminum compounds obtained by this reaction can exhibit, in general, only extremely low polymerization activity when they are used in combination with a metallocene compound. For this reason, these compounds are unsatisfactory as substitutes of alumoxane compounds, and require further improvement.

An object of the present invention is to solve the various problems accompanying the above-described prior art. Another object of the present invention is to provide a cocatalytic component useful for producing polymers having high molecular weight.

SUMMARY OF THE INVENTION

The present invention has been accomplished as a result of various studies which were made in order to solve the aforementioned problems.

The present invention provides, in one aspect thereof, a catalyst component for the polymerization of olefins which comprises a compound having the following structure:

wherein $R^1$ is a hydrocarbon radical having 1 to 10 carbon atoms, or a halogen-containing hydrocarbon radical having 1 to 10 carbon atoms and $R^2$s are each a hydrogen atom, a halogen atom, a siloxy group, a lower-alkyl-substituted siloxy group or a hydrocarbon radical having 1 to 10 carbon atoms.

Another catalyst component for the polymerization of olefins according to the present invention in another aspect thereof comprises a reaction product of the subcomponents (i) and (ii):

sub-component (i) which is a compound having the formula $$R^1-B-(OH)_2$$

in which $R^1$ is a hydrocarbon radical having 1 to 10 carbon atoms or a halogen-containing hydrocarbon radical having 1 to 10 carbon atoms; and component (ii) which is an organoaluminum compound.

The present invention provides, in still another aspect thereof, a catalyst for the polymerization of α-olefins which comprises Component (A) which is a compound having the structure of the above formula (I) or a reaction product of the above sub-components (i) and (ii), and Component (B) which is a transition-metal compound having at least one conjugated 5-membered cyclic ligand where the transition metal belongs to one of the Groups IVB to VIB in the Periodic Table.

Another catalyst for the polymerization of α-olefins according to the present invention in still another aspect thereof comprises Component (A) which is a compound having the structure of the above formula (I) or a reaction product of the above components (i) and (ii), Component (B) which is a transition-metal compound having at least one conjugated 5-membered cyclic ligand where the transition metal belongs to one of the Groups IVB to VIB in the Periodic Table, and Component (C) which is an organoaluminum compound having no boron in its molecule.

The present invention also provides in further aspect thereof a method of preparing α-olefin polymers which comprises contacting an α-olefin with a catalyst thereby to polymerize the α-olefin, said catalyst comprising Component (A) and Component (B) and optionally Component (C).

When the catalyst component for the polymerization of olefins according to the present invention is used, as the organometal component of a Ziegler catalyst, for the polymerization of olefins in combination with a transition-metal component, the catalytic activity per aluminum atom is significantly improved, whereby use is dispensed with of alumoxane which is expensive. In addition, use can be dispensed with of an aromatic hydrocarbon solvent which places restrictions on the industrial production, and polymers having a higher molecular weight can be obtained.

DETAILED DESCRIPTION OF THE INVENTION

<Catalyst Component for Polymerization of Olefins>

The catalyst component for the polymerization of olefins according to the present invention can be used, as the organometallic compound component of a Ziegler catalyst useful fop the polymerization of olefins, in combination with a transition-metal component which will be described later in detail.

The catalyst component for the polymerization of olefins according to the present invention, referred to as Component (A) comprises a compound having the following structure (I):

wherein $R^1$ is a hydrocarbon radical having 1 to 10 carbon atoms or a halogen-containing hydrocarbon radical having 1 to 10 carbon atoms, and R2s are each a hydrogen atom, a halogen atom, a siloxy group, a lower-alkyl-substituted siloxy group or a hydrocarbon radical having 1 to 10 carbon atoms. Further, the catalyst component for the polymerization of olefins according to the present invention comprises a reaction product of the subcomponents (i) and (ii):

sub-component (i) which is a compound having the formula $$R^1\text{-B-(OH)}_2$$

in which $R^1$ is a hydrocarbon radical having 1 to 10 carbon atoms or a halogen-containing hydrocarbon radical having 1 to 10 carbon atoms; and component (ii) which is an organoaluminum compound.

Compound (I)

The organoboroaluminum compound of a structure (I) given above may be prepared by the reaction of a compound of a formula $R^1\text{-B-(OH)}_2$ and an organoaluminum compound of a formula: $R^2_3Al$, or a formula: $(R^2)_2\text{-Al-O-Al-}(R^2)_2$ where $R^2$ Al $R^2$ is the same as defined in the formula (I).

The substituents $R^1$ and $R^2$ in the organoboroaluminum compound of formula (I) may thus depend on the organoboron compound and the organoaluminum compound used in its preparation.

The organoboron compound and the organoaluminum compound are used in another or a second embodiment of the present invention given above where the Component (A) is a reaction product of the compound of a formula: $R^1\text{-B-(OH)}_2$ with an organoaluminum compound in place of the organoboroaluminum compound of formula (I).

Examples of the organoboroaluminum compound of a formula (I) will thus be found in the description of the second embodiment of the present invention given hereinbelow.

Component (i)

The component (i) is a boronic acid or alternatively a dihydroxylborane represented by the general formula $R^1\text{-B-(OH)}_2$, in which $R^1$ is a hydrocarbon radical or a halogen-containing hydrocarbon radical each having 1 to 10, preferably 1 to 6, carbon atoms. More preferably, $R^1$ is a hydrocarbon radical having 1 to 6 carbon atoms. Specific examples of such an alkylboronic acid include methylboronic acid/methyldihydroxylborane, ethylboronic acid, isopropylboronic acid, n-propylboronic acid, n-butylboronic acid, isobutylboronic acid, n-hexylboronic acid, cyclohexylboronic acid, phenylboronic acid, 3,5difluorophenylboronic acid, pentafluorophenylboronic acid and 3,5-bis(trifluoromethyl)phenylboronic acid. Of these, methylboronic acid, ethylboronic acid, n-butylboronic acid, isobutylboronic acid, 3,5-difluorophenylboronic acid and pentafluorophenylboronic acid are preferred, and methylboronic acid, ethylboronic acid and n-butylboronic acid are more preferred.

Component (ii)

The component (ii) is an organoaluminum compound.

Any organoaluminum compounds may be used provided that it produces a reaction product with the organoboron compound (i) which will produce advantages inherent in the present invention.

Examples of the organoaluminum compounds as the component (ii) which are preferable in the present invention include those compounds which are represented by the general formula $(R^2)_3Al$ or $(R^2)_2Al-O-Al-(R^2)_2$, in which $R^2$ each represents a hydrogen atom, a halogen atom, a siloxy group, a lower-alkyl-substituted siloxy group or a hydrocarbon radical having 1 to 10 carbon atoms, provided that at least one $R^2$ among 3 or 4 $R^2$s is a hydrocarbon radical having 1 to 10 carbon atoms.

Specific examples of the organoaluminum compound include the following compounds: (a) trialkylaluminums such as trimethylaluminum, triethylaluminum, triisobutylaluminum, trihexylaluminum, trioctylaluminum, tridecylaluminum, tri-n-butylaluminum, tri-n-propylaluminum and triisoprenylaluminum; (b) alkylaluminum halides such as dimethylaluminum monochloride, diethylaluminum monochloride, diisobutylaluminum monochloride, methylaluminum sesquichloride, ethylaluminum sesquichloride and ethylaluminum dichloride; (c) alkylaluminum hydrides such as dimethylaluminum hydride, diethylaluminum hydride and diisobutylaluminum hydride; (d) alkylaluminum siloxides such as dimethylaluminum (trimethylsiloxide), dimethylaluminum (triethylsiloxide) and diethylaluminum (trimethylsiloxide); and (e) tetraalkyl alumoxanes such as tetraisobutyl alumoxane and tetraethyl alumoxane. It is also possible to use a mixture of a plurality of these compounds within and/or between the sub-groups (a)–(e).

Of the above organoaluminum compounds, derivatives of methylaluminum, ethylaluminum or isobutylaluminum such as trimethylaluminum, triethylaluminum, triisobutylaluminum, dimethylaluminum chloride, diisobutylaluminum chloride and diisobutylaluminum hydride are preferred. Trimethylaluminum, triethylaluminum, triisobutylaluminum and a mixture thereof are more preferred.

Contact between Components (i) and (ii)

The components (i) and (ii) can be reacted in any ratio. However, it is suitable to adjust the molar ratio of the components (i):(ii) to 1:2 in order to efficiently obtain a desired reaction product. Further, in general, the reaction between the components (i) and (ii) is carried out in an inert solvent under an inert gas atmosphere. Various methods are employable to bring the components (i) and (ii) into contact with each other. For instance, the following methods can be mentioned: (a) the method in which the component (i) is mixed in a toluene solvent, and then a solution prepared by diluting the component (ii) with toluene is added dropwise to the mixture, thereby reacting the components (i) and (ii); (b) the method in which the component (i) in the form of solid is supplied to a solution prepared by diluting the component (ii) with hexane, thereby reacting the components (i) and (ii); and (c) the method in which the components (i) and (ii) are diluted with toluene separately, and the dilute solutions are added dropwise to one vessel at an equal speed, thereby reacting the components (i) and (ii). Any reaction temperature and time can be used for the reaction between the components (i) and (ii). However, in general, the reaction proceeds rapidly and a side reaction can readily take place, so that it is preferable to employ such a method that after the both components are mixed at a low temperature, for instance, at −78° to 30° C., preferably at −78° to 10° C., the temperature of the mixture is gradually raised, for instance, to −10° to 70° C. Any reaction time can be used as long as a desired product can be obtained. In general, however, the reaction is carried out in the range of one minute to 24 hours.

<Transition-Metal Component>

The catalyst component, which will be herein referred to as Component (A), for the polymerization of olefins according to the present invention is employed as the organometal component of a Ziegler catalyst in combination with a known transition-metal component to make up the Ziegler catalyst for the polymerization of olefins. Among known transition-metal components, a transition-metal compound, which will be herein referred to as Component (B), having at least one conjugated 5-membered cyclic ligand where the transition metal belongs to one of the Groups IVB to VIB in the Periodic Table is preferably used. Specifically, transition-metal compounds represented by the following general formula (II):

$$Q_a(C_5H_{5-a-b}R^4_b)(C_5H_{5-a-c}R^5_c)MeXY \qquad (II)$$

and by the following general formula (III):

$$S_a(C_5H_{5-a-d}R^6_d)ZMeXy \qquad (III)$$

can be mentioned.

In the above formulas, Q represents a binding group or a "bridge" which crosslinks the two conjugated 5-membered cyclic ligands, and S represents a binding group or a "bridge" which crosslinks the conjugated 5-membered cyclic ligand and the group Z. Specifically, Q and S are (a) a $C_1$–$C_4$ alkylene or cyclohexylene group such as a methylene, ethylene, isopropylene, phenylmethylmethylene, diphenylmethylene or cyclohexylene group, or its derivatives having a lower alkyl- or phenyl-substituent; (b) a silylene or oligosilylene group such as a silylene, dimethylsilylene, phenylmethylsilylene, diphenylsilylene, disilylene or tetramethyldisilylene group, or its derivatives having a lower alkyl- or phenyl-substituent; or (c) a hydrocarbylated or hydrocarbyloxylated germanium, phosphorus, nitrogen, boron or aluminum, where the valence of the element is satisfied by a hydrocarbon group, preferably a lower alkyl or phenyl group, or a hydrocarbyloxy group, preferably a lower alkoxy group, provided that the valence of 2 is left for the bridging. Specifically, a $(CH_3)_2Ge$, $(C_6H_5)_2Ge$, $(CH_3)P$, $(C_6H_5)P$, $(C_4H_9)N$, $(C_6H_5)N$, $(CH_3)B$, $(C_4H_9)B$, $(C_6H_5)B$, $(C_6H_5)Al$ or ($CH_3O$)Al group; preferably a lower with or without a lower alkyl substituent alkylene or a silylene or oligosilylene group with or without a lower alkyl substituent, a is 0 or 1.

In the above general formulas, the conjugated 5-membered cyclic ligands represented by ($C_5H_{5-a-b}R^4{}_b$), ($C_5H_{5-a-c}R^5{}_c$) and ($C_5H_{5-a-b}R^6{}_d$) respectively are defined separately. However, the definitions themselves of b, c and d are the same, and those of $R^4$, $R^5$ and $R^6$ are also the same (described later in detail). It is therefore needless to say that these three conjugated 5-membered cyclic ligands may be the same or different from one another.

One specific example of the conjugated 5-membered cyclic ligand is a cyclopentadienyl group (having no substituent other than the binding group Q or S) in which b (or c or d) is 0. In the case where the conjugated 5-membered cyclic ligand is one in which b (or c or d) is not 0, thus having a substituent, a specific example of $R^4$ (or $R^5$ or $R^6$) is a $C_1$-$C_{20}$, preferably a $C_1$-$C_{12}$ hydrocarbon group. This hydrocarbon group may typically be bound to the cyclopentadienyl group as a monovalent group, but when a plurality of the hydrocarbon groups are existing, two of them may or may not be bound to each other at their respective or omega ends to form a ring along with a part of the cyclopentadienyl group. A typical example of the latter is a case where $R^4$ (or $R^5$ or $R^6$) forms a condensed 6-membered ring sharing a double bond of the cyclopentadienyl group, that is, this conjugated 5-membered cyclic group is an indenyl or fluorenyl group. Therefore, typical examples of this conjugated 5-membered cyclic group are substituted or unsubstituted cyclopentadienyl, indenyl and fluorenyl groups.

$R^4$, $R^5$ and $R^6$ are, in addition to the above-described $C_1$-$C_{20}$, preferably $C_1$-$C_{12}$ hydrocarbon group, a halogen atom (e.g., fluorine, chlorine or bromine), an alkoxy group (e.g., a $C_1$-$C_{12}$ alkoxy group), a silicon-containing hydrocarbon group (e.g., a group having approximately 1 to 24 carbon atoms, containing a silicon atom in the form of -Si(R)(R')(R'')), a phosphorus-containing hydrocarbon group (e.g., a group having approximately 1 to 18 carbon atoms, containing a phosphorus atom in the form of -P(R)(R')), a nitrogen-containing hydrocarbon group (e.g., a group having approximately 1 to 18 carbon atoms, containing a nitrogen atom in the form of -N(R)(R')) or a boron-containing hydrocarbon group (e.g., a group having approximately 1 to 18 carbon atoms, containing a boron atom in the form of -B(R)(R')). When b (or c or d) is 2 or more and a plurality of $R^4$s (or $R^5$s or $R^6$s) are existing, they may be the same or different.

b, c and d are an integer which fulfills the conditions of $0 \leq b \leq 5$, $0 \leq c \leq 5$ and $0 \leq d \leq 5$ when a is 0; and $0 \leq b \leq 4$, $0 \leq c \leq 4$ and $0 \leq d \leq 4$ when a is 1.

Me is a transition metal belonging to one of the Groups IVB to VIB in the Periodic Table, preferably titanium, zirconium and hafnium. Zirconium is particularly preferred.

Z is oxygen (-O-), sulfur (-S-), an alkoxy group having 1 to 20, preferably 1 to 10 carbon atoms, a thioalkoxy group having 1 to 20, preferably 1 to 12 carbon atoms, a silicon-containing hydrocarbon group having 1 to 40, preferably 1 to 18 carbon atoms, a nitrogen-containing hydrocarbon group having 1 to 40, preferably 1 to 18 carbon atoms, or a phosphorus-containing hydrocarbon group having 1 to 40, preferably 1 to 18 carbon atoms.

X and Y are independently a hydrogen atom, a halogen atom, a hydrocarbon group having 1 to 20, preferably 1 to 10 carbon atoms, an alkoxy group having 1 to 20, preferably 1 to 10 carbon atoms, an amino group, a phosphorus-containing hydrocarbon group having 1 to 20, preferably 1 to 12 carbon atoms (specifically, for example, a diphenylphosphine group), or a silicon-containing hydrocarbon group having 1 to 20, preferably 1 to 12 carbon atoms (specifically, for example, a trimethylsilyl group). X and Y may be the same or different. Of these, a halogen atom and a hydrocarbon group are preferred.

Specific examples of the transition-metal compound in which Me is zirconium are as follows:

(a) transition-metal compounds which have two conjugated 5-membered cyclic ligands but have no binding group for crosslinking the ligands, for instance, (1) bis(cyclopentadienyl)zirconium dichloride,
(2) bis(methylcyclopentadienyl)zirconium dichloride,
(3) bis(dimethylcyclopentadienyl)zirconium dichloride,
(4) bis(trimethylcyclopentadienyl)zirconium dichloride,
(5) bis(tetramethylcyclopentadienyl)zirconium dichloride,
(6) bis(pentamethylcyclopentadienyl)zirconium dichloride,
(7) bis(n-butylcyclopentadienyl)zirconium dichloride,
(8) bis(indenyl)zirconium dichloride,
(9) bis(fluorenyl)zirconium dichloride,
(10) bis(cyclopentadienyl)zirconium monochloride monohydride,
(11) bis(cyclopentadienyl)methylzirconium monochloride,
(12) bis (cyclopentadienyl)ethylzirconium monochloride,
(13) bis (cyclopentadienyl)phenylzirconium monochloride,
(14) bis (cyclopentadienyl)zirconium dimethyl,
(15) bis (cyclopentadienyl)zirconium diphenyl,
(16) bis (cyclopentadienyl)zirconium dineopentyl,
(17) bis (cyclopentadienyl)zirconium dihydride,
(18) bis(cyclopentadienyl)(indenyl)zirconium dichloride, and
(19) bis(cyclopentadienyl)(fluorenyl)zirconium dichloride;

(b) transition-metal compounds having two 5-membered cyclic ligands crosslinked by an alkylene group, for instance, (1) methylenebis(indenyl)zirconium dichloride,
(2) ethylenebis(indenyl)zirconium dichloride,
(3) ethylenebis(indenyl)zirconium monohydride monochloride,
(4) ethylenebis(indenyl)methylzirconium monochloride,
(5) ethylenebis(indenyl)zirconium monomethoxymonochloride,
(6) ethylenebis(indenyl)zirconium diethoxide,
(7) ethylenebis(indenyl)zirconium dimethyl,
(8) ethylenebis(4,5,6,7-tetrahydroindenyl)zirconium dichloride,
(9) ethylenebis(2-methylindenyl)zirconium dichloride,
(10) ethylenebis(2-ethylindenyl)zirconium dichloride,
(11) ethylenebis(2,4-dimethylindenyl)zirconium dichloride,
(12) ethylenebis (2-methyl-4-trimethylsilylindenyl)zirconium dichloride,
(13) ethylene(2,4-dimethyl-5,6,7-trihydroindenyl)zirconium dichloride, (14) ethylene(2,4-dimethylcyclopentadienyl)(3',5'-dimethylcyclopentadienyl)zirconium dichloride,
(15) ethylene(2-methyl-4-tert-butylcyclopentadienyl)(3-tert-butyl-5'-methylcyclopentadienyl)zirconium dichloride,
(16) ethylene(2,3,5-trimethylcyclopentadienyl)(2',4',5'-trimethylcyclopentadienyl)zirconium dichloride,
(17) isopropylidenebis(2-methylindenyl)zirconium dichloride,
(18) isopropylidenebis(indenyl)zirconium dichloride,
(19) isopropylidenebis(2,4-dimethylindenyl)zirconium dichloride,
(20) isopropylidene(2,4-dimethylcyclopentadienyl)(3',5'-dimethylcyclopentadienyl)zirconium dichloride,
(21) isopropylidene(2-methyl-4-tert-butylcyclopentadienyl) (3'-tert-butyl-5'-methylcyclopentadienyl)zirconium dichloride,
(22) methylene(cyclopentadienyl)(3,4-dimethylcyclopentadienyl)zirconium dichloride,
(23) methylene(cyclopentadienyl) (3,4-dimethylcyclopentadienyl)zirconium chloride hydride,
(24) methylene(cyclopentadienyl) (3,4-dimethylcyclopentadienyl)zirconium dimethyl,
(25) methylene(cyclopentadienyl) (3,4-dimethylcyclopentadienyl)zirconium diphenyl,
(26) methylene(cyclopentadienyl) (trimethylcyclopentadienyl)zirconium dichloride,
(27) methylene(cyclopentadienyl) (tetramethylcyclopentadienyl)zirconium dichloride,
(28) isopropylidene(cyclopentadienyl)(3,4-dimethylcyclopentadienyl)zirconium dichloride,
(29) isopropylidene(cyclopentadienyl)(2,3,4,5-tetramethylcyclopentadienyl)zirconium dichloride,
(30) isopropylidene(cyclopentadienyl)(3methylindenyl)zirconium dichloride,
(31) isopropylidene(cyclopentadienyl)(fluorenyl)zirconium dichloride,
(32) isopropylidene(2-methylcyclopentadienyl)(fluorenyl)zirconium dichloride,
(33) isopropylidene(2,5-dimethylcyclopentadienyl)(3,4-dimethylcyclopentadienyl)zirconium dichloride,
(34) isopropylidene(2,5-dimethylcyclopentadienyl)(fluoro)zirconium dichloride,
(35) ethylene(cyclopentadienyl)(3,5-dimethylcyclopentadienyl)zirconium dichloride,
(36) ethylene(cyclopentadienyl)(fluorenyl)zirconium dichloride,
(37) ethylene(2,5-dimethylcyclopentadienyl)(fluorenyl)zirconium dichloride,
(38) ethylene(2,5-diethylcyclopentadienyl)(fluorenyl)zirconium dichloride,
(39) diphenylmethylene(cyclopentadienyl)(3,4-diethylcyclopentadienyl)zirconium dichloride,
(40) diphenylmethylene(cyclopentadienyl)(3,4-diethylcyclopentadienyl)zirconium dichloride,
(41) cyclohexylidene(cyclopentadienyl)(fluorenyl)zirconium dichloride, and
(42) cyclohexylidene(2,5-dimethylcyclopentadienyl)(3',4'-dimethyldimethylcyclopentadienyl)zirconium dichloride;
(c) transition-metal compounds having 5-membered cyclic ligands crosslinked by a silylene group, for instance,
(1) dimethylsilylenebis(indenyl)zirconium dichloride,
(2) dimethylsilylenebis(4,5,6,7-tetrahydroindenyl)zirconium dichloride,
(3) dimethylsilylenebis(2-methylindenyl)zirconium dichloride,
(4) dimethylsilylenebis(2,4-dimethylindenyl)zirconium dichloride,
(5) dimethylsilylene(2,4-dimethylcyclopentadienyl)(3',5'-dimethylcyclopentadienyl)zirconium dichloride,
(6) phenylmethylsilylenebis(indenyl)zirconium dichloride,
(7) phenylmethylsilylenebis(4,5,6,7-tetrahydroindenyl)zirconium dichloride,
(8) phenylmethylsilylenebis(2,4-dimethylindenyl)zirconium dichloride,
(9) phenylmethylsilylene(2,4-dimethylcyclopentadienyl)(3',5'-dimethylcyclopentadienyl)zirconium dichloride,
(10) phenylmethylsilylene(2,3,5-trimethylcyclopentadienyl)(2',4',5'-trimethylcyclopentadienyl)zirconium dichloride,
(11) phenylmethylsilylenebis(tetramethylcyclopentadienyl)zirconium dichloride,
(12) diphenylsilylenebis(2,4-dimethylindenyl)zirconium dichloride,
(13) diphenylsilylenebis(indenyl)zirconium dichloride,
(14) diphenylsilylenebis(2-methylindenyl)zirconium dichloride,
(15) tetramethyldisilylenebis(indenyl)zirconium dichloride,
(16) tetramethyldisilylenebis(cyclopentadienyl)zirconium dichloride,
(17) tetramethyldisilylene(3-methylcyclopentadienyl)(indenyl)zirconium dichloride,
(18) dimethylsilylene(cyclopentadienyl)(3,4-dimethylcyclopentadienyl)zirconium dichloride,
(19) dimethylsilylene(cyclopentadienyl)(trimethylcyclopentadienyl)zirconium dichloride,
(20) dimethylsilylene(cyclopentadienyl)(tetramethylcyclopentadienyl)zirconium dichloride,
(21) dimethylsilylene(cyclopentadienyl)(3,4-diethylcyclopentadienyl)zirconium dichloride,
(22) dimethylsilylene(cyclopentadienyl)(triethylcyclopentadienyl)zirconium dichloride,
(23) dimethylsilylene(cyclopentadienyl)(tetraethylcyclopentadienyl)zirconium dichloride,
(24) dimethylsilylene(cyclopentadienyl)(fluorenyl)zirconium dichloride,
(25) dimethylsilylene(cyclopentadienyl)(2,7-di-t-butylfluorenyl)zirconium dichloride,
(26) dimethylsilylene(cyclopentadienyl)(octahydrofluorenyl)zirconium dichloride,
(27) dimethylsilylene(2-methylcyclopentadienyl)(fluorenyl)zirconium dichloride,
(28) dimethylsilylene(2,5-dimethylcyclopentadienyl)(fluorenyl)zirconium dichloride,
(29) dimethylsilylene(2-ethylcyclopentadienyl)(fluorenyl)zirconium dichloride,
(30) dimethylsilylene(2,5-diethylcyclopentadienyl) (fluorenyl)zirconium dichloride,
(31) diethylsilylene(2-methylcyclopentadienyl)(2,7-di-t-butylfluorenyl)zirconium dichloride,
(32) dimethylsilylene(2,5-dimethylcyclopentadienyl)-(2,7-di-t-butylfluorenyl)zirconium dichloride,
(33) dimethylsilylene(2-ethylcyclopentadienyl)-(2,7-di-t-butylfluorenyl)zirconium dichloride,
(34) dimethylsilylene(diethylcyclopentadienyl)-(2,7-di-t-butylfluorenyl)zirconium dichloride,
(35) dimethylsilylene(methylcyclopentadienyl)(octahydrofluorenyl)zirconium dichloride, (36) dimethylsilylene(dimethylcyclopentadienyl)(octahydrofluorenyl)zirconium dichloride,
(37) dimethylsilylene(ethylcyclopentadienyl)(octahydrofluorenyl)zirconium dichloride, and
(38) dimethylsilylene(diethylcyclopentadienyl)(octahydrofluorenyl)zirconium dichloride;

(d) transition-metal compounds having 5-membered cyclic ligands crosslinked by a hydrocarbon group containing germanium, aluminum, boron, phosphorus or nitrogen, for instance,
(1) dimethylgermaniumbis(indenyl)zirconium dichloride,
(2) dimethylgermanium(cyclopentadienyl)(fluorenyl)zirconium dichloride,
(3) dimethylaluminumbis(indenyl)zirconium dichloride,
(4) phenylaluminumbis(indenyl)zirconium dichloride,
(5) phenylphosphinobis(indenyl)zirconium dichloride,
(6) ethylboranobis(indenyl)zirconium dichloride,
(7) phenylaminobis(indenyl)zirconium dichloride, and
(8) phenylamino(cyclopentadienyl)(fluorenyl)zirconium dichloride;

(e) transition-metal compounds having one 5-membered cyclic ligand, for instance,
(1) (pentamethylcyclopentadienyl)bis(phenyl)amidozirconium dichloride,
(2) (indenyl)-bis(phenyl)amidozirconium dichloride,
(3) (pentamethylcyclopentadienyl)bis(trimethylsilyl)amidozirconium dichloride,
(4) (pentamethylcyclopentadienyl)phenoxyzirconium dichloride,
(5) dimethylsilylene(tetramethylcyclopentadienyl)-(t-butylamido)zirconium dichloride,
(6) dimethylsilylene(tetramethylcyclopentadienyl)phenylamidozirconium dichloride,
(7) dimethylsilylene(tetrahydroindenyl)decylamidozirconium dichloride,
(8) dimethylsilylene(tetrahydroindenyl)trimethylsilylamidozirconium dichloride, and
(9) dimethylgerman(tetramethylcyclopentadienyl)phenylaminozirconium dichloride; and (f) those compounds which are obtained by replacing chlorine in the above compounds (a) to (e) with bromine, iodine, hydride, methyl, phenyl or the like.

Further, in the present invention, any of those compounds which are obtained by changing the central metal of the zirconium compounds enumerated in the above (a) to (f) to titanium, hafnium, niobium, molybdenum or tungsten can also be used as the transition-metal component, the Component (B).

Of these, zirconium, hafnium and titanium compounds are preferred, and titanium, zirconium and hafnium compounds in which the ligands are crosslinked by an alkylene or silylene group are more preferred.

<Optional Component>

The catalyst component for the polymerization of olefins according to the present invention, viz. Component (A), is useful as a Ziegler-type polymerization catalyst when the above-described transition-metal component, viz. Component (B), is used in combination. Components other than the Components (A) and (B) can also be optionally used unless they unduly mar the effects of the present invention. Optional components which can be added include active hydrogen-containing compounds such as H₂O, methanol, ethanol and butanol, electron-donor compounds such as an ether, an ester and an amine, alkoxy-containing compounds such as phenyl borate, dimethylmethoxyaluminum, phenylphosphite, tetraethoxysilane and diphenyldimethoxysilane, and organoboron compounds such as triethylborane, triphenylborane, tris(pentafluorophenyl)borane and triphenylcarbyltetrakis(pentafluorophenyl)borate.

The catalyst component for the polymerization of olefins according to the present invention, Component (A), is useful for making up a catalyst for the polymerization of α-olefins not only when it is combined with the above-described transition-metal component, Component (B), but also when it is further combined, in addition to Component (B), with an organoaluminum compound having no boron in its molecule which will be referred to as Component (C).

Specific examples of such an organoaluminum compound having no boron atom, Component (C), include compounds represented by the formula of $R^7_{3-n}AlX_n$ or $R^8_{3-m}Al(OR^9)_m$, wherein $R^7$ and $R^8$, which may be the same or different, are a hydrocarbon radical having approximately 1 to 20 carbon atoms or a hydrogen atom, $R^9$ is a hydrocarbon radical having approximately 1 to 20 carbon atoms, X is halogen, and n and m are a number of $0 \leq n < 3$ and $0 < m < 3$, respectively; and compounds represented by the following general formula (II) or (III):

in which p is a number which is 0 to 40, preferably 2 to 25, and $R^{10}$ represents a hydrocarbon radical, preferably one having 1 to 10 carbon atoms, particularly one having 1 to 4 carbon atoms.

Specifically, the following compounds can be mentioned as the organoaluminum compound:

(a) trialkylaluminums such as trimethylaluminum, triethylaluminum, triisobutylaluminum, trihexylaluminum, trioctylaluminum and tridecylaluminum;
(b) alkylaluminum halides such as diethylaluminum monochloride, diisobutylaluminum monochloride, ethylaluminum sesquichloride and ethylaluminum dichloride;
(c) alkylaluminum hydrides such as diethylaluminum hydride and diisobutylaluminum hydride;
(d) aluminum alkoxides such as diethylaluminum ethoxide, dimethylaluminum trimethylsiloxide and diethylaluminum phenoxide; and
(e) alkylalumoxanes such as methylalumoxane, ethylalumoxane, isobutylalumoxane and methylisobutylalumoxane. It is also possible to use a mixture of two or more of the above compounds between and/or within the groups (a)–(e). Of these compounds, trialkylaluminums and aluminum alkoxides are preferred. Those organoaluminum compounds which have a methyl, ethyl or isobutyl group are more preferred.

<Formation of Catalyst>

The catalyst component, Component (A), according to the present invention will make up a catalyst for the polymerization of olefins when it is brought into contact with the above-described Component (B) and optionally Component (C), and, if necessary, a further optional component within or outside of a polymerization vessel, in the presence or absence of a monomer to be polymerized.

In the case where the catalyst composed of the above Components (A) and (B) is used for polymerization, these components can be used in any amount. However, in general, their amounts are determined so that the atomic ratio (Al/Me) of the aluminum atom in Component (A) to the transition metal atom (Me) in Component (B) will be from 0.01 to 100,000, preferably from 0.1 to 30,000, more preferably from 2 to 10,000. These components can be brought into contact with each other by any method, for instance, the components can be separately introduced and brought into contact with each other when polymerization is conducted; or they can be brought into contact with each other in advance and used for polymerization.

In the case where the catalyst composed of the above Components (A), (B) and (C) is used for polymerization, these components can be used in any amount. However, in general, the amount of the organoaluminum compound, Component (A), is such that the atomic ratio (Al/Me) of the aluminum atom in Component (A) to the transition metal atom in the Component (B) will be from 0.01 to 100,000, preferably from 0.1 to 10,000, more preferably from 2 to 3,000. Further, the atomic ratio of (Al/Me) of the aluminum atom in the organoaluminum compound, Component (C), to the transition metal atom (Me) in Component (B) is from 0.01 to 10,000, preferably from 0.1 to 1,000. These components can be brought into contact with one another by any method, for instance, the components can be separately introduced into a polymerization vessel in any order and brought into contact with one another when polymerization is conducted; or any two of the components can be brought into contact with each other in advance, introduced into a polymerization vessel, and brought into contact with the other component.

<Polymerization of α-Olefins>

The catalyst component or catalyst according to the present invention can be employed not only for solvent polymerization using a solvent but also for polymerization using substantially no solvent such as liquid-phase non-solvent polymerization, gas-phase polymerization or solution polymerization. It can also be used for either continuous or batch-wise polymerization.

A saturated aliphatic or aromatic hydrocarbon solvent such as hexane, heptane, pentane, cyclohexane, benzene or toluene can be used either singly or in combination as a solvent for solvent polymerization.

The polymerization temperature is approximately −78° to 200° C., preferably −20° to 100° C. There is no particular limitation on the olefin pressure of a reaction system. However, the pressure is preferably in the range of from atmospheric pressure to 50 kg/cm$^2$-G. Further, the molecular weight can be controlled by a known technique, such as the selection of the temperature or pressure, or the introduction of hydrogen.

An α-olefin, including ethylene in the present invention, which polymerizes upon contact with the catalyst of the present invention, that is, an α-olefin which is used for the polymerization reaction in the method according to the present invention is an α-olefin having 2 to 20, preferably 2 to 10 carbon atoms. Specific examples of such an α-olefin include ethylene, propylene, 1-butene, 4-methyl-1-pentene, 1-hexene, 1-octene, 1-decene, 1-dodecene, 1-tetradecene, 1-hexadecene, 1-octadecene and 1-eicocene. Of these, ethylene, propylene, 1-butene, 1-hexene and 4-methyl-1- pentene are particularly preferred. It is also possible to use a mixture of two or more of these α-olefins for polymerization.

Further, it is also possible to copolymerize any of the above α-olefins and ethylene by the use of the catalyst of the present invention. Moreover, the catalyst of the present invention is also useful for the copolymerization of any of the above α-olefins and another copolymerizable monomer, for example, a conjugated or unconjugated diene such as butadiene, 1,4hexadiene, 1,8-nonadiene, 7-methyl-1,6-octadiene or 1,9-decadiene, or a cyclic olefin such as cyclopropene, cyclobutene, cyclopentene, norbornene or dicyclopentadiene.

The present invention will now be described more specifically by referring to Examples and Comparative Examples. However, the following examples should not be construed as limiting the present invention.

<Example 1>

Preparation of Component (A).

Bis(diisobutylaluminumoxy)methylboran was synthesized in accordance with the following procedure:

Specifically, to a 500 ml flask purged with nitrogen were introduced 100 ml of n-hexane which had been thoroughly dehydrated and deoxygenated and 3.0 g (50 mmol) of methylboronic acid manufactured by Aldrich Company, and the mixture was cooled to below −50° C. Thereafter, 19.8 g (100 mmol) of triisobutylaluminum diluted with 100 ml of n-hexane was gradually added dropwise to the mixture over 30 minutes. During the addition, the reaction temperature was maintained at no higher than −50° C. After the addition was completed, the temperature of the resulting mixture was gradually raised to 0° C. over one hour. During this process, the mixture gradually generated gas when its temperature reached nearly −10° C., and thus the reaction proceeded. As the reaction proceeded, the solid methylboronic acid was dissolved. The reaction mixture was kept at 0° C. for two hours and then warmed to room temperature to terminate the reaction. After the reaction was completed, the solvent was distilled off under reduced pressure. As a result, approximately 17 g of a liquid compound, viz. Catalyst component (A-1), was obtained. The aluminum compound thus obtained was diluted with toluene, and the dilute solution was subjected to an 27Al-NMR analysis. As a result, a broad peak with a half band width of 12,800 Hz appeared at 134.9 ppm (see FIG. 1).

Figure 1:
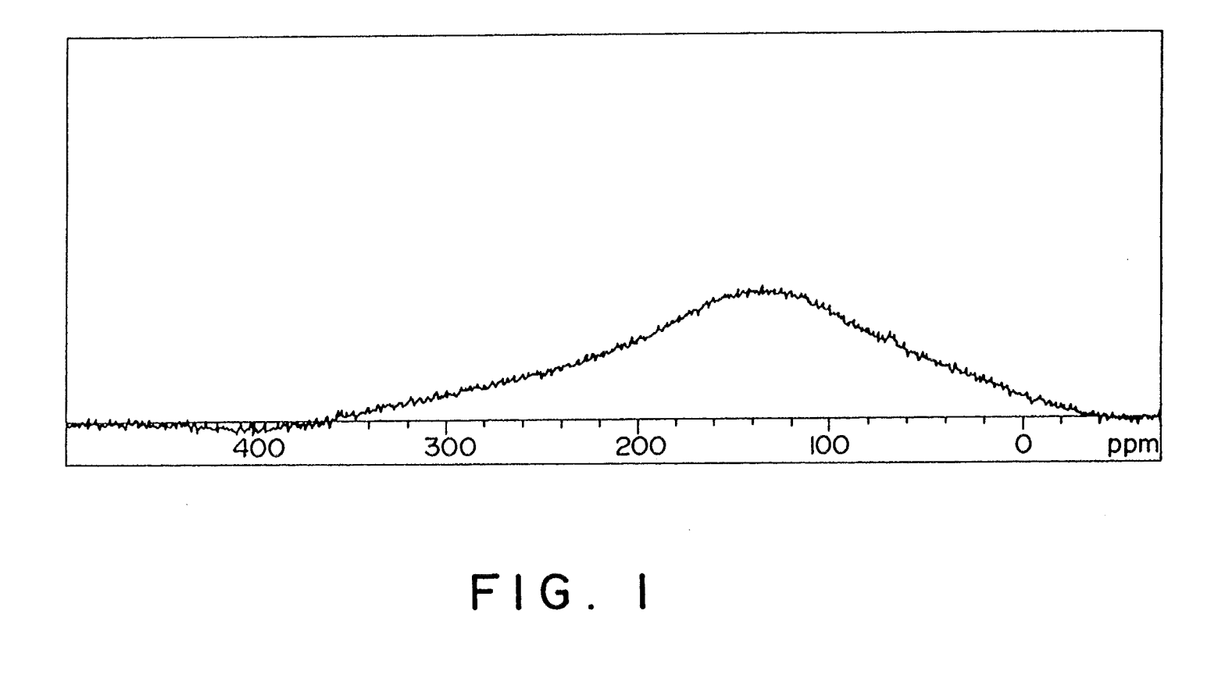
FIG. 1 is a chart showing the $^{27}$Al-NMR spectrum of the bis(diisobutylaluminoxy)methylboran prepared in Example 1.

It is noted that the NMR spectrum (27Al: 70.4 MHz) was measured on a mixture of 2.5 ml of a toluene solution containing 6 to 7% by weight (aluminum atom basis) of the aluminum compound and 0.5 ml of benzene-D$_6$, and subjecting the mixture to the measurement conducted at 27° C., using an NMR spectrometer, the model GSX-270 manufactured by JEOL Ltd. The conditions for the measurement of the 27Al-NMR spectrum were as follows: the pulse angle was 90°, the pulse delay was 0.06 seconds, the integration number was 10000 times, non-decoupling mode was adopted, and an [Al(-H$_2$O)$_6$]$^{3+}$ ion in an aqueous solution of aluminum sulfate was used as an outer standard (0 ppm) for the $^{27}$Al chemical shift. the half band width of the spectrum was obtained in Hz from the peak width at half of the maximum height of the peak.

Preparation of Component (B)

Dimethylsilylenebis(tetrahydroindenyl)zirconium dichloride was synthesized in accordance with J. Orgmet. Chem. (342) 21–29, 1988 and J. Orgmet. Chem. (369) 359–370, 1989.

More particularly, in a 300 ml flask purged with nitrogen, 5.4 g of bis(indenyl)dimethylsilane was diluted with 150 ml of tetrahydrofuran, and the resulting solution was cooled to below $-50°$ C. Thereafter, 23.6 ml of n-butyl lithium (1.6 M/L) was added dropwise to the solution over 30 minutes. After the addition was completed, the temperature of the mixture was raised to room temperature over one hour, and a reaction was carried out at room temperature for 4 hours to synthesize a reaction solution A.

200 ml of tetrahydrofuran was introduced to a 500 ml flask purged with nitrogen, and cooled to below $-50°$ C. To this was gradually introduced 4.38 g of zirconium tetrachloride. Subsequently, the entire quantity of the reaction solution A was introduced, and the temperature of the resulting mixture was gradually raised to room temperature over 3 hours. After a reaction was carried out at room temperature for 2 hours, the reaction mixture was further warmed to 60° C., and the reaction was carried out at the temperature for 2 hours. After the reaction was completed, the solvent was distilled off under reduced pressure, and the residue was dissolved in 100 ml of toluene. The solution was subjected to distillation again to obtain 3.86 g of crude crystals of dimethylsilylenebis(indenyl)zirconium dichloride.

Subsequently, the crude crystals were dissolved in 150 ml of dichloromethane, and the solution was introduced to a 500 ml autoclave. After 5 g of a platinum-carbon catalyst (0.5% by weight of platinum being supported on carbon) was introduced to the solution, a hydrogenation reaction was carried out under the conditions of an $H_2$ pressure of 50 kg/cm$^2$G and 50° C. for 5 hours. After the reaction was completed, the catalyst was filtered off, and the solvent was distilled off. The residue was subjected to extraction with toluene, and then recrystallized, thereby obtaining 1.26 g of a desired compound, dimethylsilylenebis(tetrahydroindenyl)zirconium dichloride.

Polymerization of Ethylene

To a stainless-steel autoclave with an internal volume of 1.5 liters, thoroughly purged with ethylene gas, and equipped with a stirrer and a temperature controller, 500 ml of toluene which had been thoroughly dehydrated and deoxygenated and 2 mmol (aluminum atom basis) of the above-synthesized Catalyst component (A-1) of the present invention were introduced. Subsequently, 0.91 mg (2 micromol) of the above-synthesized dimethylsilylenebis(tetrahydroindenyl)zirconium dichloride was added, and 100 ml of hydrogen was then introduced to the mixture. The temperature of the resulting mixture was raised, and polymerization was conducted under the conditions of 75° C. and 7 kg/cm$^2$G for 2 hours. After the polymerization was completed, the resulting slurry was placed in 3 liters of ethanol. A polymeric material was separated from the mixture by filtration, and then dried. As a result, 53.5 g of a polymer was obtained. Therefore, the catalytic activity was 58.7 kg polymer/g-Component (B). The MI at 190° C. was found to be 178.8 g/10 minutes. The melting point of the polymer determined by DSC was 131.5° C.

<Example 2>

Polymerization of Ethylene

Ethylene was polymerized under the conditions of Example 1 except that the amount of Component (A-1) was changed to 6 mmol (aluminum atom basis). The results are shown in Table 1.

<Example 3>

Figure 2:
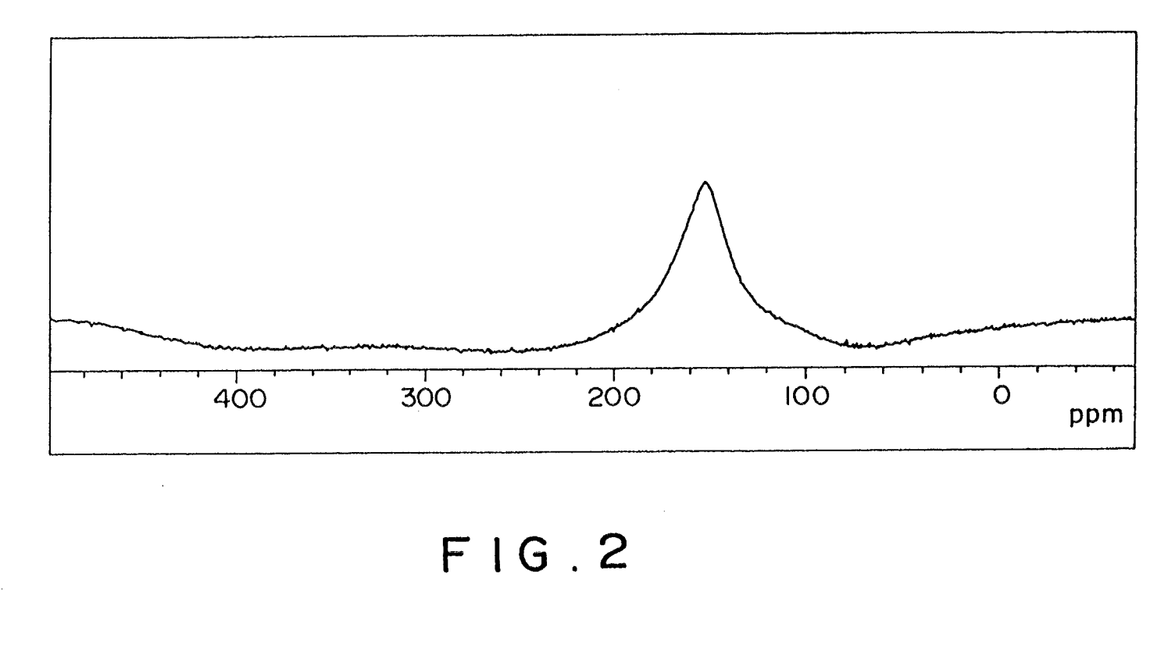
FIG. 2 is a chart showing the $^{27}$Al-NMR spectrum of the bis(dimethylaluminumoxy)methylboran prepared in Example 3.

Bis(dimethylaluminumoxy)methylboran (A-2) was synthesized in accordance with the procedure of Example 1 except that 7.2 g of trimethylaluminum diluted with 100 ml of toluene was used instead of 19.8 g of the triisobutylaluminum used in the preparation of Component (A) in Example 1. A chart showing the $^{27}$Al-NMR spectrum of the reaction product [bis(dimethylaluminumoxy)methylboran] is shown in FIG. 2.

Polymerization of Ethylene

Ethylene was polymerized under the conditions of Example 1 except that 2 mmol (aluminum atom basis) of the above-obtained Component (A-2) was used. The results are shown in Table 1.

<Examples 4–7>

Preparation of Component (A)

Component (A) was synthesized under the conditions of Example 3 except that the sub-components (i) and (ii) used were changed as shown in Table 2.

Polymerization of Ethylene

By using the above Component (A), ethylene was polymerized in accordance with the procedure of Example 1. The results are shown in Table 2.

<Example 8>

Copolymerization of Ethylene/1-Hexene

To a stainless steel-made autoclave with an internal volume of 1.5 liters, thoroughly purged with ethylene gas, and equipped with a stirrer and a temperature controller, 500 ml of toluene which had been thoroughly dehydrated and deoxygenated, 60 ml of 1-hexene, and 2 mmol (aluminum atom basis) of the catalytic component (A-1) synthesized in Example 1 were introduced. Subsequently, 1 micromole of the dimethylsilylenebis(tetrahydroindenyl)zirconium dichloride synthesized in Example 1 was added to the mixture. The temperature of the resulting mixture was raised, and polymerization was conducted under the conditions of 75° C. and 7 kg/cm$^2$G for 2 hours. After the polymerization was completed, the reaction solution was placed in 3 liters of ethanol. The precipitated polymeric material was separated by filtration, and then dried to obtain 51.3 g of a polymer. Therefore, the catalytic activity was 112.5 kg polymer/g-Component (B). The MI at 190° C. was 0.11 g/10 minutes, and the melting point of the polymer was 101.2° C. The polymer was subjected to a measurement using 13C-NMR Spectroscopy, and, as a result, the hexene content of the polymer was found to be 6.5 mol %. The copolymer obtained had a molecular weight which was higher (i.e., the MI of the copolymer was lower) than that of polymers obtained by the use of known alumoxane.

\<Example 9\>

Preparation of Component (B)

Preparation of dimethylsilylenebis(tetrahydroindenyl)zirconium dimethyl:

To a 300 ml flask thoroughly purged with nitrogen were introduced 100 ml of diethyl ether which had been thoroughly dehydrated and deoxygenated and 0.912 g of the dimethylsilylenebis(tetrahydroindenyl)zirconium dichloride obtained in Example 1, and the mixture was cooled to below −50° C. Subsequently, 4 ml (6 mmol) of a 1.5 M solution of methyl lithium diluted with diethyl ether was diluted again with 10 ml of diethyl ether, and the resulting solution was fed to the mixture over 15 minutes. After the feeding was completed, the temperature of the mixture was raised to −10° C. over one hour, and a reaction was carried out by further raising the temperature to 10° C. over two hours. After the reaction was completed, the diethyl ether was distilled off at a temperature of 0° to 10° C. Subsequently, 50 ml of n-pentane which had been dehydrated and deoxygenated was added to the residue, and the mixture was stirred for 10 minutes. The solvent was distilled off to such a degree that a supernatant liquid which would be obtained after the removal of a solid matter by filtration became approximately 10 ml, and the residue was allowed to stand in a refrigerator over one night to obtain white crystals. The crystals were separated, washed with a small amount of pentane, and then dried. As a result, 0.65 g of dimethylsilylenebis (tetrahydroindenyl ) zirconium dimethyl was obtained.

Polymerization of Propylene

To a stainless-steel autoclave with an internal volume of 1.5 liters, thoroughly purged with propylene gas, and equipped with a stirrer and a temperature controller, 500 ml of toluene which had been thoroughly dehydrated and deoxygenated, and 2 mmol of Component (A5) obtained in Example 6 were introduced. Subsequently, 0.84 mg (2/μmol ) of the above-obtained dimethylsilylenebis (tetrahydroindenyl ) zirconium dimethyl was introduced to the mixture, and polymerization was conducted under the conditions of 70° C. and 7 kg/cm$^2$G for 2 hours. After the polymerization was completed, the resulting slurry was placed in 3 liters of methanol to thoroughly precipitate a polymeric material. This material was separated by filtration, and then dried to obtain 6.7 g of a polymer. Therefore, the catalytic activity was 7.8 kg polymer/g-Component (B). The number average molecular weight of the polymer was 15,600,the molecular-weight distribution (weight-average molecular weight/number-average molecular weight) was 1.88, and the melting point of the polymer was 123° C.

\<Example 10\>

Preparation of Component (B).

Synthesis of dimethylsilylene(tetramethylcyclo-pentadienyl)tert-butylamidotitanium dichloride:

In a 300 ml flask thoroughly purged with nitrogen was placed 100 ml of tetrahydrofuran (THF) which had been dehydrated and deoxygenated. 2.52 g (10 mmol) of (tert-butylamide)(tetramethylcyclopentadienyl)dimethylsilane manufactured by Kanto Chemical Co., Inc. was dissolved in the THF. Subsequently, the solution was cooled to below −50° C., and 13.4 ml (20 mmol) of a 1.5 M solution of methyl lithium diluted with diethyl ether was introduced to the solution over 10 minutes. The temperature of the mixture was raised to room temperature over one hour, and a reaction was carried out at room temperature for 6 hours. After the reaction was completed, the solvent was distilled off, and the residue was washed several times with THF, thereby obtaining 2.16 g of dilithium(tert-butylamide)(tetramethylcyclopentadienyl) dimethylsilane.

Subsequently, in a 300 ml flask thoroughly purged with nitrogen, 100 ml of diethyl ether which had been dehydrated and deoxygenated and 0.38 g (2 mmol) of titanium tetrachloride were mixed at a temperature of −50° C. or lower. To this mixture, 2 mmol (0.53 g) of the above-obtained dilithium(tert-butylamide)-(tetramethylcyclopentadienyl)dimethylsilane diluted with 10 ml of tetrahydrofuran was added dropwise at a temperature of −50° C. or lower over 30 minutes. After the addition was completed, the temperature of the mixture was raised to room temperature over one hour, and a reaction was carried out at room temperature for a whole day and night. After the reaction was completed, the solvent was distilled off, and 50 ml of toluene was added to the residue. The mixture was filtered to remove the lithium chloride, and the toluene was then evaporated. 30 ml of n-pentane was added to the residue to obtain a solution which was preserved in a refrigerator for a whole day and night. As a result, 0.25 g of a desired compound, dimethylsilylene(tetramethylcyclopentadienyl)-tert-butylamidotitanium dichloride, was obtained as yellow crystals.

Polymerization of Ethylene

Ethylene was polymerized under the conditions of Example 1 except that the above Component (B) was used. As a result, 18.7 g of a polymer was obtained. Therefore, the catalytic activity was 25.4 kg polymer/g-Component (B). The MI was 97 g/10 minutes, and the melting point of the polymer was 132.1° C.

TABLE 1

| | Component (A) | Amount used (Al atom basis) | Amount of Polymer (g) | Catalytic activity | | MI 190° C. (g/10 min) | Melting Point (°C.) |
|---|---|---|---|---|---|---|---|
| | | | | Kg polymer/g Component (B) | g polymer/g-Al | | |
| Example 1 |  | 2 mmol | 53.5 | 58.7 | 991 | 178.8 | 131.5 |

TABLE 1-continued

| | Component (A) | Amount used (Al atom basis) | Amount of Polymer (g) | Catalytic activity Kg polymer/g Component (B) | Catalytic activity g polymer/-g-Al | MI 190° C. (g/10 min) | Melting Point (°C.) |
|---|---|---|---|---|---|---|---|
| Example 2 |  | 0.6 mmol | 62.6 | 68.6 | 3864 | 86.8 | 132.1 |

TABLE 2

| | | Component (A) | | | $^{27}$Al-NMR Spectrum (ppm) | Yield (g) | Catalytic activity (Kg polymer/g-Component (B)) | MI 190° C. (g/10 min) |
|---|---|---|---|---|---|---|---|---|
| | Abb. | Component (i) | Component (ii) | Conditions for reaction | | | | |
| Example 3 | A-2 | Methylboronic acid 50 mmol | Trimethyl-aluminum 100 mmol | Fed at −50° C., raised the temperature for 1 hour, reacted at 0° C. for 2 hours | 152 | 47.2 | 51.7 | 116.4 |
| Example 4 | A-3 | Ethylboronic acid 50 mmol | Triisobutyl-aluminum 100 mmol | Fed at −50° C., raised the temperature for 1 hour, reacted at 0° C. for 2 hours | 139.5 | 8.2 | 9.0 | 45.0 |
| Example 5 | A-4 | Phenylboronic acid 50 mmol | Triisobutyl-aluminum 100 mmol | Fed at −50° C., raised the temperature for 1 hour, reacted at 0° C. for 2 hours | 151.2 | 5.2 | 5.7 | unmeasurable |
| Example 6 | A-5 | Methylboronic acid 50 mmol | Trimethyl-aluminum 50 mmol Triisobutyl-aluminum 50 mmol | Fed at −50° C., raised the temperature for 1 hour, reacted at 0° C. for 2 hours | 137.2 | 33.1 | 36.3 | 46.5 |
| Example 7 | A-6 | Methylboronic acid 50 mmol | Tetraisobutyl-alumoxane 200 mmol (Al atom basis) | Fed at −50° C., reacted at 0° C. for 2 hours and at 50° C. for 2 hours | 38.7/ 62.5 | 18.8 | 20.6 | 60 |

<Example 11>

Preparation of Component (A)

Bis(diisobutylaluminumoxy)methylboran was synthesized in the same manner as in Example 1.

Preparation of Component (B)

Dimethylsilylenebis(tetrahydroindenyl)zirconium dichloride was synthesized in the same manner as in Example 1.

Polymerization of Ethylene

To a stainless-steel autoclave with an internal volume of 1.5 liters, thoroughly purged with ethylene gas, and equipped with a stirrer and a temperature controller, 500 ml of toluene which had been thoroughly dehydrated and deoxygenated, 2 mmol (aluminum atom basis) of the above-synthesized Component (A−1) according to the present invention, and 36 mg of trimethylaluminum were introduced. Subsequently, 0.91 mg (2 μmol) of the above-synthesized dimethylsilylenebis(tetrahydroindenyl)zirconium dichloride was added, and 100 ml of hydrogen was introduced to the mixture. The temperature of the mixture was raised, and polymerization was conducted under the conditions of 75° C. and 7 kg/cm²G for 2 hours. After the polymerization was completed, the resulting slurry was placed in 3 liters of ethanol. A polymeric material was separated by filtration and then dried, thereby obtaining 110.3 g of a polymer. Therefore, the catalytic activity was 120.9 kg polymer/g-Component (B). The MI at 190° C. was found to be 536 g/10 minutes.

<Example 12>

Ethylene was polymerized under the conditions of Example 11 except that the amounts of the trimethylaluminum and the Component (A-1) were changed to 7.2 mg and 1 mmol, respectively. The results are shown in Table 3. <Comparative Example 1>

Ethylene was polymerized under the conditions of Example 11 except that Component (A-1) was not used. The results are shown in Table 3.

<Comparative Examples 2 and 3>

Figure 3:
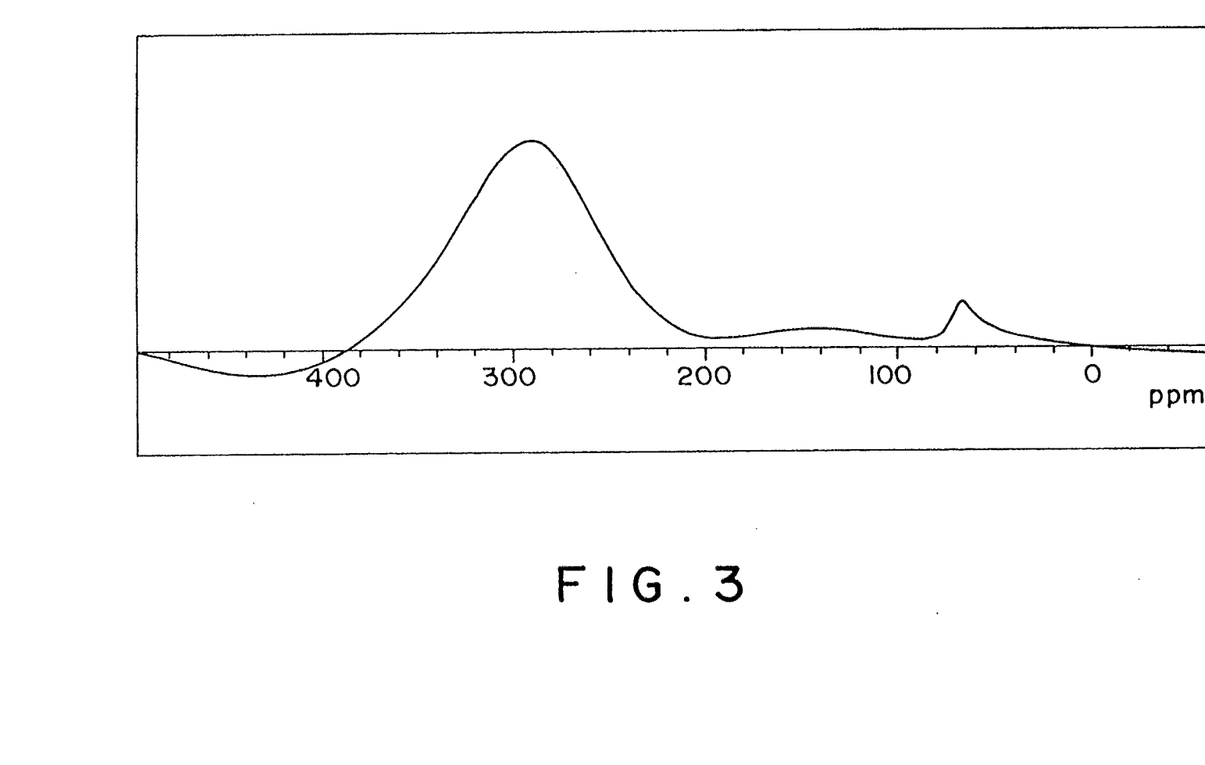
FIG. 3 is a chart showing the $^{27}$Al-NMR spectrum of the tetraisobutylalumoxane (manufactured by Schering Company) used in Comparative Example 2.
Figure 4:
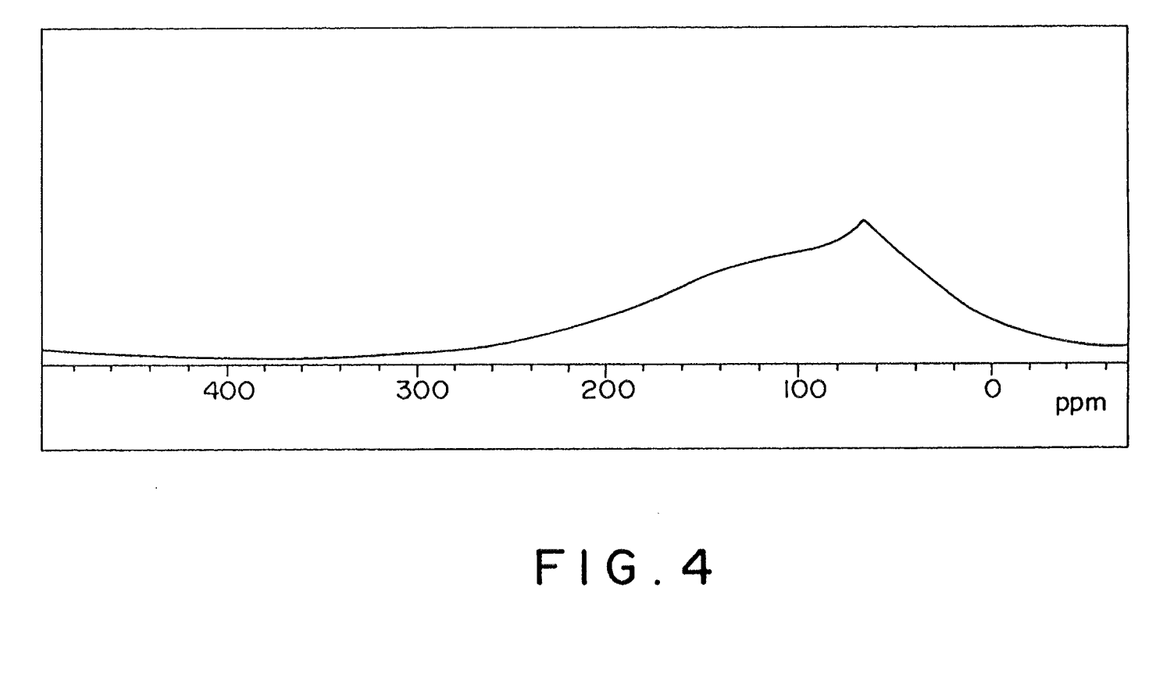
FIG. 4 is a chart showing the $^{27}$Al-NMR spectrum of the polyisobutylalumoxane (manufactured by Toso-Akzo Co., Ltd.) used in Comparative Example 3.

Ethylene was polymerized under the conditions of Example 11 except that tetraisobutylalumoxane (manufactured by Schering Company) or polyisobutylalumoxane (manufactured by Toso-Akzo Co., Ltd.) was used instead of Component (A-1). The results are shown in Table 3. Charts showing the 27Al-NMR spectra of the tetraisobutylalumoxane and the polyisobutylalumoxane are shown in FIG. 3 and FIG. 4, respectively.

<Examples 13 and 14>

Ethylene was polymerized under the conditions of Example 12 except that 33.7 mg of triethylaluminum or 59.4 mg of triisobutylaluminum were used instead of 36 mg of the trimethylaluminum. The results are shown in Table 3.

<Example 15>

Bis(dimethylaluminumoxy)methylboran (A-2) was synthesized in accordance with the procedure of Example 1 except that 7.2 g of trimethylaluminum diluted with 100 ml of toluene was used instead of 19.8 g of the triisobutylaluminum used for the preparation of Component (A) in Example 1. A chart showing the 27Al-NMR spectrum of the bis(dimethylaluminumoxy)methylboran (A-2) is shown in FIG. 2.

Polymerization of Ethylene

Ethylene was polymerized under the conditions of Example 11 except that 2 mmol (aluminum atom basis) of the above-obtained Component (A-2) was used.

As a result, 95.5 g of a polymer was obtained. Therefore, the catalytic activity was 104.7 kg polymer/g-Component (B), and the activity per aluminum atom was 1,410 g polymer/g-Al atom. The MI was found to be 388 g/10 minutes.

<Example 16>

Preparation of Component (B)

Preparation of dimethylsilylenebis(tetrahydroindenyl)zirconium dimethyl:

To a 300 ml flask thoroughly purged with nitrogen were introduced 100 ml of diethyl ether which had been thoroughly dehydrated and deoxygenated and 0.912 g of the dimethylsilylenebis(tetrahydroindenyl)zirconium dichloride obtained in Example 1, and the mixture was cooled to below −50° C. Subsequently, 4 ml (6 mmol) of a 1.5 M solution of methyl lithium diluted with diethyl ether was diluted again with 10 ml of diethyl ether, and the resulting solution was fed to the above mixture. After the feeding was completed, the temperature of the resulting mixture was raised to −10° C. over one hour, and a reaction was carried out while the temperature was further raised to 10° C. over 2 hours. After the reaction was completed, the diethyl ether was distilled off at a temperature of 0° to 10° C. 50 ml of n-pentane which had been dehydrated and deoxygenated was added to the residue, and the mixture was stirred for 10 minutes. The solvent was distilled off to such a degree that a supernatant liquid which would be obtained after the removal of a solid matter became approximately 10 ml, and the residue was allowed to stand in a refrigerator over one night to obtain white crystals. The crystals were separated, washed with a small amount of pentane, and then dried. As a result, 0.65 g of dimethylsilylenebis(tetrahydroindenyl)zirconium dimethyl was obtained.

Polymerization of Propylene

To a stainless-steel autoclave with an internal volume of 1.5 liters, thoroughly purged with propylene gas, and equipped with a stirrer and a temperature controller, 500 ml of toluene which had been thoroughly dehydrated and deoxygenated, 2 mmol of the same Component (A-1) as was used in Example 11, and 36.0 mg of trimethylaluminum were introduced. Subsequently, 0.84 mg (2 μmol) of the above-obtained dimethylsilylenebis(tetrahydroindenyl)zirconium dimethyl was introduced into the mixture, and polymerization was conducted under the conditions of 70° C. and 7 kg/cm²G for 2 hours. After the polymerization was completed, the resulting slurry was placed in 3 liters of methanol to thoroughly precipitate a polymeric material. This material was separated by filtration, and then dried, thereby obtaining 22.3 g of a polymer. Therefore, the catalytic activity was 24.4 kg polymer/g-Component (B). The number-average molecular weight of the polymer was 12,600, the molecular-weight distribution (weight-average molecular weight/number-average molecular weight) was 1.95, and the melting point of the polymer was 121° C.

<Example 17>

Preparation of Component (A)

Component (A) was prepared as in Example 1 except that 9.9 g of triisobutylaluminum and 3.6 g of trimethylaluminum which had been mixed and diluted with 100 ml of toluene were used instead of 19.8 g of the triisobutylaluminum used for the preparation of Component (A) in Example 1. As a result, 12.2 g of a liquid compound (A-3) was obtained.

Polymerization of Propylene

Propylene was polymerized under the conditions of Example 16 except that 2 mmol of the above-obtained compound (A-3) was used. The results are shown in Table 4.

<Examples 18 and 19>

Propylene was polymerized under the conditions of Example 17 except that 34.3 mg of triethylaluminum or 59.4 mg of triisobutylaluminum was used instead of 36.0 mg of the trimethylaluminum used for the polymerization of propylene in Example 17. The results are shown in Table 4.

<Example 20>

Preparation of Component (B)

Synthesis of dimethylsilylene(tetramethylcyclo-pentadienyl)tert-butylamidotitanium dichloride:

In a 300 ml flask thoroughly purged with nitrogen was placed 100 ml of tetrahydrofuran (THF) which had been dehydrated and deoxygenated. 2.52 g (10 mmol) of (tert-butylamido)(tetramethylcyclopentadienyl)-dimethyl silane manufactured by Kanto Chemical Co., Inc. was dissolved in the THF. Subsequently, the solution was cooled to below −50° C., and to this was then introduced 13.4 ml (20 mmol) of a 1.5 M solution of methyllithium diluted with diethyl ether over 10 minutes. The temperature of the mixture was raised to room temperature over one hour, and a reaction was carried out at room temperature for 6 hours. After the reaction was completed, the solvent was distilled off, and the residue was washed several times with THF, thereby obtaining 2.16 g of dilithium(tert-butylamido)(tetramethylcyclopentadienyl) dimethylsilane.

Subsequently, in a 300 ml flask thoroughly purged with nitrogen, 100 ml of diethylether which had been dehydrated and deoxygenated and 0.38 g (2 mmol) of titanium tetrachloride were mixed at a temperature of −50° C. or lower. To this mixture, 2 mmol (0.53 g) of the above-obtained dilithium(tert-butylamido)(tetramethylcyclopentadienyl)dimethylsilane diluted with 10 ml of tetrahydrofuran was added dropwise at a temperature of −50° C. or lower over 30 minutes. After the addition was completed, the temperature of the mixture was raised to room temperature over one hour, and a reaction was conducted at room temperature for a whole day and night. After the reaction was completed, the solvent was distilled off, and 50 ml of toluene was added to the residue. The mixture was filtered to remove the lithium chloride, and the toluene was then evaporated. 30 ml of n-pentane was added to the residue to obtain a solution which was preserved in a refrigerator for a whole day and night. As a result, 0.25 g of a desired compound, dimethylsilylene(tetramethylcyclopentadienyl)-tert-butylamidotitanium dichloride, was obtained as yellow crystals.

Polymerization of Ethylene

Ethylene was polymerized under the conditions of Example 11 except that the above Component (B) was used. As a result, 33.8 g of a polymer was obtained. Therefore, the catalytic activity was 45.9 kg polymer/g-Component (B). The MI was 152 g/10 minutes, and the melting point of the polymer was 132.0° C.

obtained above, 0.3 mmol of triisobutylaluminum, 0,456 mg (1 μM) of dimethylsilylenebis(tetrahydroindenyl)-zirconium dichloride and 50 cc of hydrogen were used.

The result obtained is set forth in Table 5.

<Example 22>

Preparation of Component (A)

To a 500 ml flask purged with nitrogen were introduced 100 ml of toluene which had been thoroughly dehydrated and deoxygenated and 2 g (19.6 mM) of n-butylboric acid manufactured by Aldrich Company, and the mixture was cooled to −50° C. Thereafter,

TABLE 3

| | Component (C) | | Component (A) | | Yield of Polymer (g) | Catalytic Activity | | MI (190° C.) g/10 min |
|---|---|---|---|---|---|---|---|---|
| | Type | mg (mmol) | | Amount used Al atom basis | | Kg polymer/g Component (B) | g polymer/g Al atom | |
| Example 11 | Trimethyl-aluminum | 36.0 (0.5 mmol) | Bis(diisobutyl-aluminoxy)methylboran | 2 mmol | 110.3 | 120.9 | 1,630 | 536 |
| Example 12 | ↓ | 7.2 (0.1 mmol) | ↓ | 1 mmol | 92.4 | 101.3 | 3,110 | 195 |
| Comparative Example 1 | ↓ | 36.0 (0.5) | none | | | no activity | | |
| Comparative Example 2 | Trimethyl-aluminum | 36.0 (0.5) | Tetraisobutyl-alumoxane | 2 mmol | 55.7 | 61.1 | 823 | 385 |
| Comparative Example 3 | ↓ | 36.0 | Polyisobutyl-alumoxane | 2 mmol | 5.8 | 6.4 | 86 | not measured |
| Example 13 | Triethyl-aluminum | 34.3 (0.3 mmol) | Bis(diisobutyl-aluminoxy)methylboran | 2 mmol | 99.3 | 108.9 | 1,600 | 238 |
| Example 14 | Triisobutyl-aluminum | 59.4 (0.3 mmol) | ↓ | 2 mmol | 79.3 | 87.0 | 1,280 | 309 |

TABLE 4

| | Component (C) | | Component (A) | | Yield of polymer (g) | Catalytic activity | | Melting point of polymer (°C.) | Number-average Molecular weight (Mn) |
|---|---|---|---|---|---|---|---|---|---|
| | Type | Amount mg (mmol) | | | | Kg polymer/g Component (B) | g polymer g-Al | | |
| Example 16 | Trimethylaluminum | 36.0 (0.5) | A-1 | 2 mmol | 22.3 | 24.4 | 330 | 121 | 12,600 |
| Example 17 | Trimethylaluminum | 36.0 | A-3 | ↓ | 44.5 | 53.0 | 660 | 122 | 13,500 |
| Example 18 | Triethylaluminum | 34.3 | A-3 | ↓ | 24.7 | 29.4 | 400 | 121 | 12,500 |
| Example 19 | Triisobutylaluminum | 59.4 (0.3) | A-3 | ↓ | 30.3 | 36.1 | 490 | 222 | 13,800 |

<Example 21>

Preparation of Component (A)

To a 500 ml flask purged with nitrogen were introduced 100 ml of n-heptane which had been thoroughly dehydrated and deoxygenated and 2 g (19.6 mM) of n-butylboric acid manufactured by Aldrich Company, and the mixture was cooled to −50° C. Thereafter, 65 ml (39.2 mM) of triethylaluminum diluted with heptane (0.6 mole/lit.) was gradually added dropwise to the mixture over 30 minutes. After the addition was completed, the temperature of the resulting mixture was gradually raised to room temperature over 3 hours. During this process, the mixture gradually generated gas when its temperature reached nearly −20° C. The reaction mixture was kept at room temperature for two hours. As a result, bis(diethylaluminoxy)n-butylboran desired was obtained.

Polymerization of Ethylene

Ethylene was polymerized under the conditions of Example 11 except that 1 mmol of Component (A)

ethyl was gradually added dropwise to the mixture over 30 minutes. After the addition was completed, the temperature of the resulting mixture was gradually raised to room temperature over 3 hours. The reaction mixture was kept at room temperature for two hours. As a result, Component (A) desired was obtained.

Polymerization of Ethylene

Ethylene was polymerized under the conditions of Example 21 except that 1 mmol of Component (A) obtained above, was used.

The result obtained is set forth in Table 5.

<Examples 23 and 24>

Polymerization of Propylene

Propylene was polymerized under the conditions of Example 16 except that 2 mmol of Component (A) obtained in Example 21 or 22, 0.3 mmol of triisobutylaluminum, and 0.4 micromole of dimethylsilylenebis(tetrahydroindenyl)zirconium dichloride were used.

The result obtained is set forth in Table 6.

TABLE 5

| | Component (A)*1 (based on Al atom) | Component (C)*2 | Component (B)*3 | Catalytic activity Kg-polymer/ g-Component (B) | Catalytic activity g-polymer/ g-Al atom | MI (190° C.) |
|---|---|---|---|---|---|---|
| Example 21 | A reaction product of n-butylboronic acid with triethylaluminum in 1:2 mole ratio: 1 mmol | TIBA 0.3 mmol | MSi(THI)ZrCl 1 μmol | 164.0 | 2,130 | 6.20 |
| Example 22 | A reaction product of n-butylboronic acid with triethylaluminum and triisobutylaluminum in 1:0.5:1.5 mole ratio: 1 mmol | ↓ | ↓ | 205.2 | 2,670 | 19.2 |

TABLE 6

| | Component (A) (based on Al atom) | Component (C) | Component (B) | Catalytic activity Kg-polymer/ g-Component (B) | Catalytic activity g-polymer/ g-Al atom | Polymer melting point (°C.) | Number-average molecular weight, Mn |
|---|---|---|---|---|---|---|---|
| Example 23 | A reaction product of n-butylboronic acid with triethylaluminum in 1:2 mole ratio: 2 mmol | TIBA 0.3 mmol | MSi(THI)ZrCl 4 μmol | 43.2 | 1,280 | 127 | 16,100 |
| Example 24 | A reaction product of n-butylboronic acid with triethylaluminum and triisobutylaluminum in 1:0.5:1.5 mole ratio: 2 mmol | ↓ | ↓ | 64.7 | 1,920 | 128 | 16,600 |

*2 TIBA: Triisobutylaluminum
*3 MSi(THI)ZrCl: Dimethylsilylene(tetrahydroindenyl)zirconium dichloride By the present invention, the catalytic activity per aluminum atom can be drastically improved, and it becomes unnecessary to use an alumoxane compound which is expensive and an aromatic hydrocarbon solvent which places restrictions on the industrial production, as has been previously described in the section "Summary of the Invention".

What is claimed is:

1. A catalyst component for the polymerization of olefins, comprising a compound having the following structure:

$$R^2\text{—}Al\text{—}O\text{—}B(R^1)\text{—}O\text{—}Al\text{—}R^2 \quad (I)$$

wherein $R^1$ is a hydrocarbon radical having 1 to 10 carbon atoms or a halogen-containing hydrocarbon radical having 1 to 10 carbon atoms, and $R^2$s are each a hydrogen atom, a halogen atom, a siloxy group, a lower-alkyl-substituted siloxy group or a hydrocarbon radical having 1 to 10 carbon atoms.

2. A catalyst for the polymerization of α-olefins, comprising the following Components (A) and (B):

Component (A) which is a compound having the structure as defined in claim 1; and Component (B) which is a transition-metal compound having at least one conjugated 5-membered cyclic ligand where the transition metal belongs to one of the Groups IVB to VIB in the Periodic Table.

3. A catalyst for the polymerization of α-olefins, comprising the following Components (A), (B) and (C):

Component (A) which is a compound having the structure as defined in claim 1,

Component (B) which is a transition-metal compound having at least one conjugated 5-membered cyclic ligand where the transition metal belongs to one of the Groups IVB to VIB in the Periodic Table, and Component (C) which is an organoaluminum compound other than the compound as defined as Component (A).

* * * * *